United States Patent [19]

Conlee et al.

[11] Patent Number: 4,671,010

[45] Date of Patent: Jun. 9, 1987

[54] DEVICE FOR INSECT CONTROL

[76] Inventors: Janet K. Conlee, 12126 Ashe Rd., Bakersfield, Calif. 93313; Robert T. Staten, 1662 East Manhatton Dr., Tempe, Ariz. 85282

[21] Appl. No.: 927,275

[22] Filed: Nov. 4, 1986

Related U.S. Application Data

[63] Continuation-in-part of Ser. No. 252,992, Apr. 10, 1981.

[51] Int. Cl.[4] .................. A01M 1/02; A01M 1/20
[52] U.S. Cl. ................................. 43/114; 43/131
[58] Field of Search .............. 43/114, 131; 424/84, 424/327

[56] References Cited

U.S. PATENT DOCUMENTS

| | | | |
|---|---|---|---|
| 2,157,449 | 5/1939 | Berg | 43/131 |
| 2,911,756 | 11/1959 | Geary | 43/114 |
| 3,699,111 | 10/1972 | Kaugars | 546/332 |
| 3,745,215 | 7/1973 | Kaugars | 424/327 |
| 3,996,270 | 12/1976 | Friedman | 424/84 |
| 4,017,030 | 4/1977 | Coplan et al. | 239/44 |
| 4,027,420 | 6/1977 | McKibben et al. | 43/131 |
| 4,349,981 | 9/1982 | Sherman | 43/131 |

FOREIGN PATENT DOCUMENTS 50-24858  8/1975  Japan ................................ 43/114

Primary Examiner—M. Jordan
Attorney, Agent, or Firm—Kane, Dalsimer, Kane, Sullivan and Kurucz

[57] ABSTRACT

The disclosure is of an improved device for the control of selected insect populations. The device comprises a body of a synthetic, polymeric resin adapted to contain and controllably release a pheromone of the sex attracting type. An insecticidal coating is on at least a portion of the outside surface of the resin body. Attracted insects make contact with the insecticide coating and are thereby killed or incapacitated in regard to mating.

3 Claims, 7 Drawing Figures

FIG.1
FIG.2
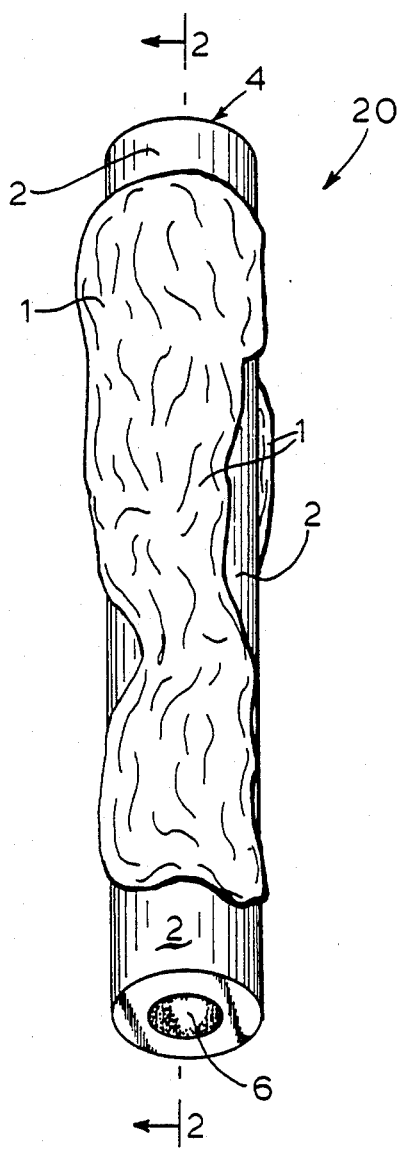
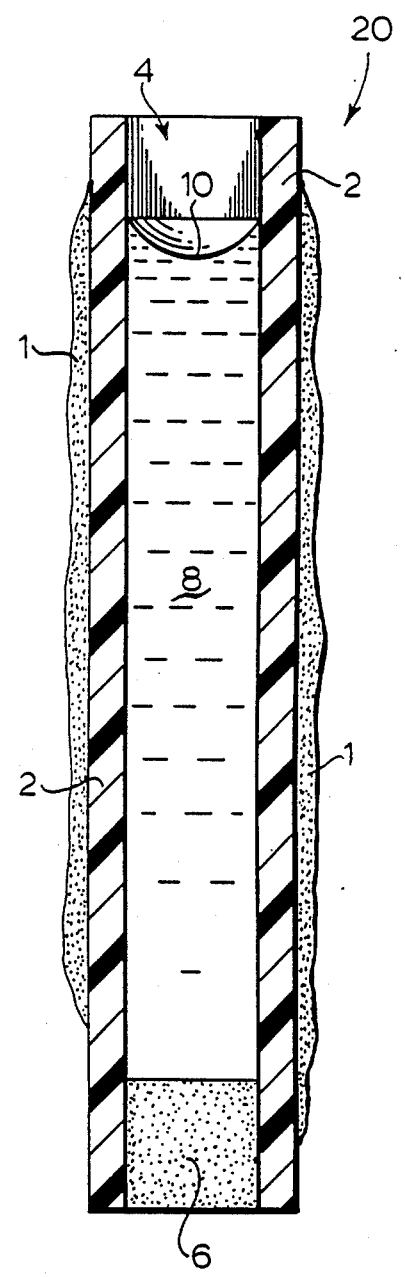

Comparison of infestation in treated and untreated plots

Comparison of infestation in treated and untreated plots

DEVICE FOR INSECT CONTROL

BACKGROUND OF THE INVENTION

The invention described herein was made in the course of or under a grant providing partial funding from the U.S. Department of Agriculture and the U.S. government has rights to this invention pursuant to U.S. Department of Agriculture case No. P.C. 6754.

CROSS-REFERENCE TO RELATED APPLICATION

This application is a continuation-in-part of our co-pending application Ser. No. 252,992 filed on Apr. 10, 1981.

1. Field of the Invenion

The invention relates to methods and devices for killing insects and more particularly relates to devices for attracting and killing selected insects.

2. Brief Description of the Prior Art

Representative of the prior art are the descriptions found in U.S. Pat. Nos. 3,016,329; 3,501,566; 3,732,282; 3,755,563; 4,017,030; 4,075,320; and 4,227,333. Among the non-patent literature, the disclosure by Del Deterling in the February 1977 issue of Progressive Farmer at page 107 is representative.

In general, sex attractant types of pheromones have been used to lure responsive insects to a designated situs where an insecticide or insect trap has been located. However, most of the prior art methods and devices have operated by the use of relatively large quantities of insecticides, usually distributed over relatively large areas. Such quantities and distributions are wasteful of material and in some cases impact undesirably against the environment.

The devices and methods of the present invention minimize area distribution of insecticides and the quantity of insecticide required for maximum effect on the insect population in a given situs. This high degree of efficiency is saving of money, labor and the environment and is complimentary to the technique of mating disruption as an insect control method.

SUMMARY OF THE INVENTION

The invention comprises, in a device for attracting selected insects to a predetermined situs, which comprises;

a body of a synthetic, polymeric resin for the containment of a pheromone which is an attractant for one of the male and the female sex gender of the selected insects;

said pheromone, contained within the body; and means for the controlled release of the pheromone from containment, in the form of a vapor, at a rate so as to attract the one of the male and female insect;

the improvement, which comprises;

a coating on at least a portion of the outside of the body, of an insecticidally effective amount of an insecticide for the insects.

The term "insecticidally effective amount" as used in the specification and claims means an amount which is lethal for an exposed insect or at least sublethal but sufficient to incapacitate the insect in regard to mating activity.

BRIEF DESCRIPTION OF THE DRAWINGS

FIG. 1 is an isometric view of a preferred embodiment, improved device of the invention.

FIG. 2 is a view along lines 2—2 of FIG. 1.

DETAILED DESCRIPTION OF THE PREFERRED EMBODIMENTS OF THE INVENTION

Figure 3:
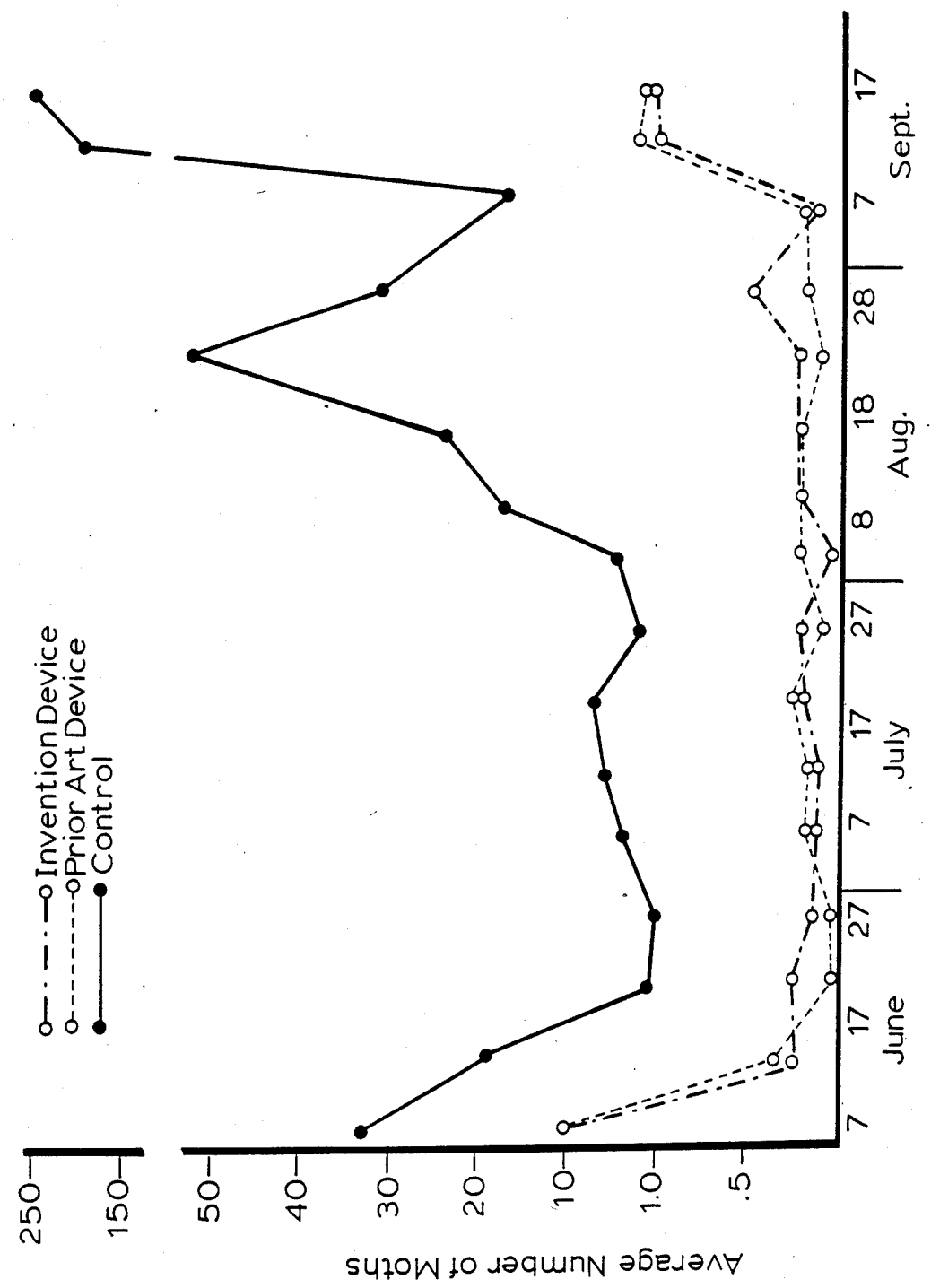
FIGS. 3-6 are graphical representations of insect counts taken at various times and under various conditions to exemplify the invention.

Those skilled in the art will gain an appreciation of the invention from the following discussion when read in conjunction with a viewing of the accompanying drawings of FIGS. 1-6, inclusive.

FIG. 1 of the accompanying drawings is an isometric view of a preferred embodiment device 20 of the invention. The device 20 comprises a capillary tubular filament 2 which has a bore of lumen 4 closed at one end by means such as heat sealing or a plug 6 of, for example, epoxy cement or like material. The device 20 includes an adhesive coating 1 on at least a portion of the outside of the filament 2. The adhesive coating 1 adheres device 20 to leaf or plant parts while at the same time being insufficient to adhere insects to the coating and contains an insecticidally effective amount of an insecticide.

Further details of the device 20 may be seen in FIG. 2, a cross-sectional side elevation as viewed along lines 2—2 of FIG. 1. As shown in FIG. 2, the lumen 4 of filament 2 is loaded with a sex attractant type of pheromone 8. The pheromone 8 preferably has a wetting type of meniscus 10 at its open end, in respect to the material of which filament 2 is fabricated. The pheromone 8 is vaporizable and vapors thereof are released through the open end of the filament 2 at a controlled rate, determined by the nature of the pheromone 8 and the surface area of the meniscus 10. The device 20, without the coating 1 component is a prior art device. The device 20, without the coating 1 may be manufactured by known methods and techniques; see for example U.S. Pat. No. 4,017,030.

The device 20 with coating 1 component is an improved device of the invention, improved by the presence of the insecticidal coating 1. The coating 1 may be affixed to the outer surface of the filament 2 by any of the conventional coating techniques, such as by dipping, spraying, brushing and like coating techniques.

The filament 2 is advantageously fabricated from a synthetic, polymeric resin. Representative of such resins are polyolefins such as polyethylene, polypropylene and the like; polyacrylics, polyesters such as polyethylene terephthalate; polyamides and the like. Preferably, biodegradable resins are employed.

The pheromone 8 is selected from the many known pheromones, dependent on the insect to be attracted and killed by the method of the invention. Sex pheromones for attracting a wide variety of insects are well known as is their preparation; see for example the text Insect Sex Pheromones, M. Jacobson, Academic Press, N.Y., N.Y. (1972) and An Annotated Compendium of Insect Sex Pheromones, Mayer and McLaughlin, Florida Agricultural Experiment Stations Monograph Series, Number 6, Institute of Food and Agricultural Sciences, University of Florida, Gainesville, Fla. (August 1975).

The insecticide coating 1 is selected on the basis of one which is effective to kill the insect, for which pheromone 8 is an attractant. Those insecticides which are effective for a given insect and the lethal dosages required are generally well known to those skilled in the art or may be determined by trial and error techniques; see for example U.S. Pat. Nos. 3,699,111 and 3,745,215.

In a preferred embodiment device of the invention, the coating 1 of insecticide is a composition which includes a "sticking agent". The term "sticking agent" as used herein means a compound or a composition which will serve to adhere the device 20 to the leaves or foliage of plants and other vegetation such as trees. Sticking agents are well known and have been used in the prior art to adhere filament materials to vegetation; see Deterling, supra. Preferred as a sticking agent ingredient in the insecticide coatings 1 are adhesive compositions of polybutene resins and the like.

The method of the invention is carried out by dispersing the devices 20 at a situs or locale infected with the selected insects which are attracted by pheromone 8 and killed or incapacitated by contact with the insecticidal coating 1. The insects attracted by pheromone 8 vapors released from the device 20 make frequent physical contact with the device. This physical contact, particularly with the outer coating 1, exposes them to lethal or sublethal doses of the insecticide, which results in their death. If, for example, the pheromone 8 is an attractant for the males of the species of insect selected, a portion of the males at the situs will be killed. The reproductive cycle of the insect species will therefore be interfered with and the insect population suppressed.

Figure 7:
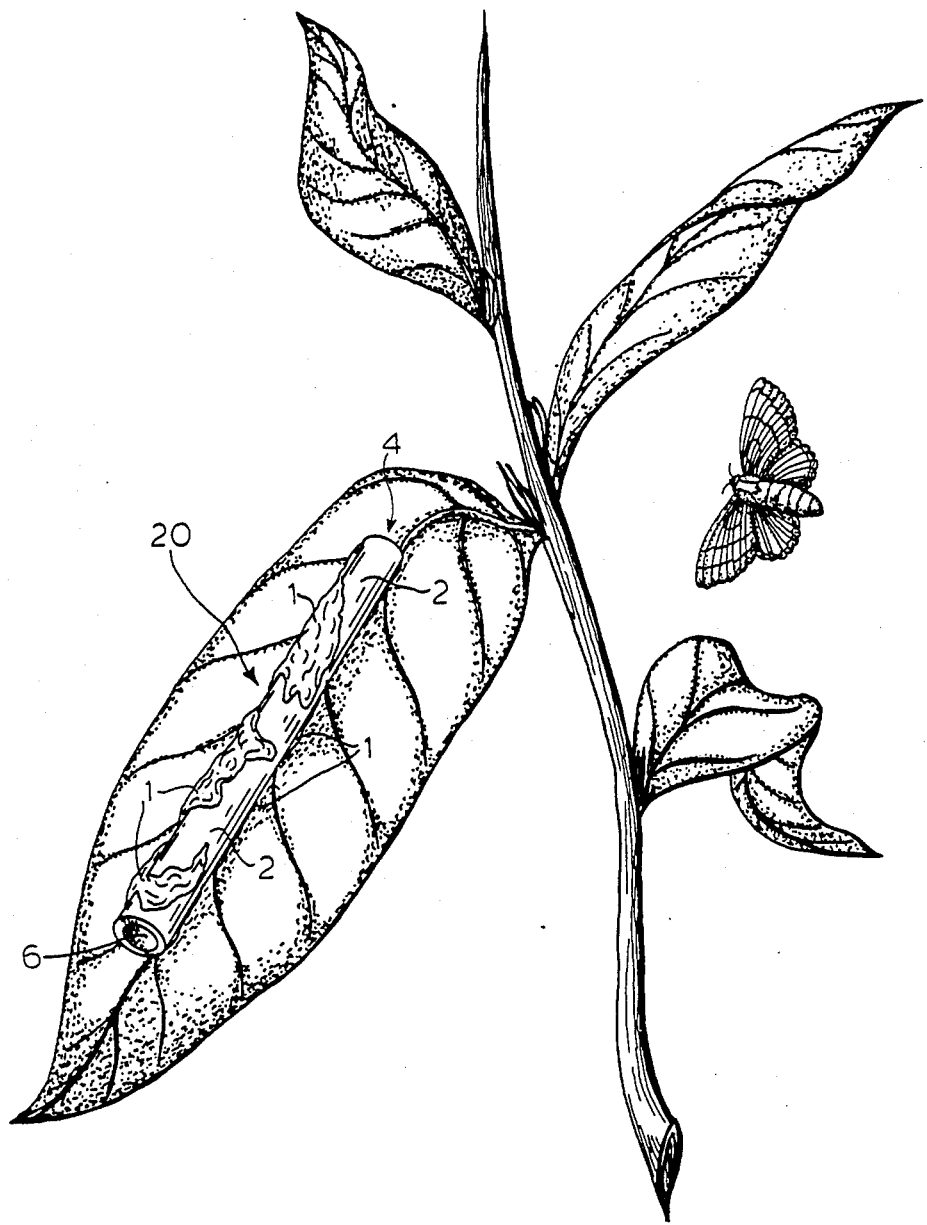
FIG. 7 is a view of the device of FIG. 1 shown in use.

FIG. 7 is an enlarged view of the device shown in FIG. 1, adhered to the leaf of a plant.

The following examples describe the manner and process of making and using the invention and set forth the best mode contemplated by the inventor of carrying out the invention, but are not to be construed as limiting the scope of the invention.

EXAMPLE 1

A quantity of polyester micro-tubes are provided, which are fabricated according to the method of U.S. Pat. No. 4,017,030 and filled with a 1:1 mixture of (Z,Z)-7,11- and (Z,E)-7,11-hexadecadien-1-ol acetate, the pheromone of the pink bollworm (*Pectinophora gossypiella*) attractive to the male of the species (Nomate, Controlled Release Division, Albany International, Albany, N.Y.). A portion of the filled tubes are coated with a mixture of 0.005 mls of an insecticide lethal to the pink bollworm (Ambush, I.C.I. Ltd.; 0.001 gms of active ingredient) in 5 gms of an emulsion of polybutene (Biotac 3, Chevron Inc.). A further portion of the filled tubes are coated with the polybutene emulsion alone as a control.

Ranch cotton fields in the area of Lone Butte, Arizona, were divided into a series of approximately 40 acre treatment plots and randomly selected for treatment by application of the coated micro-tubes. Six plots were treated with a dispersion of the micro-tubes coated with the mixture of sticking agent and insecticide (referred to hereinafter as "inventive device") and six plots were treated with a dispersion of the controls (referred to hereinafter as the "prior art device") Three adjacent plots, totalling 120 acres, were left untreated except for conventional insecticide treatments for comparison with the above treatment types (control). The distribution of inventive and prior art devices was made such that it is calculated that the treatments were made using 20 grams of Nomate and 3 pintes of Bio-tac per acre. In plots with Ambush the amount used was 0.28 oz/acre or 0.0044 lbs. a.i/ acre. A total of eight treatments were made through the cotton growing season approximately two weeks apart.

Five delta type pheromone traps were placed in each forty acre treatment plot (or a total of 30 for each treatment type and 15 for the untreated plots) for monitoring male pink bollworm moth flights. These traps were checked every day from June to October.

Mating table tests were conducted twice weekly from June through September. There were three tables in each plot. On alternate test nights all of the check plots and half of the treatment plots were used. Each night nine laboratory reared virgin females were placed on the tables with one wing clipped. The females were recollected before sunrise and disected for the presence of spermatophores.

Figure 4:
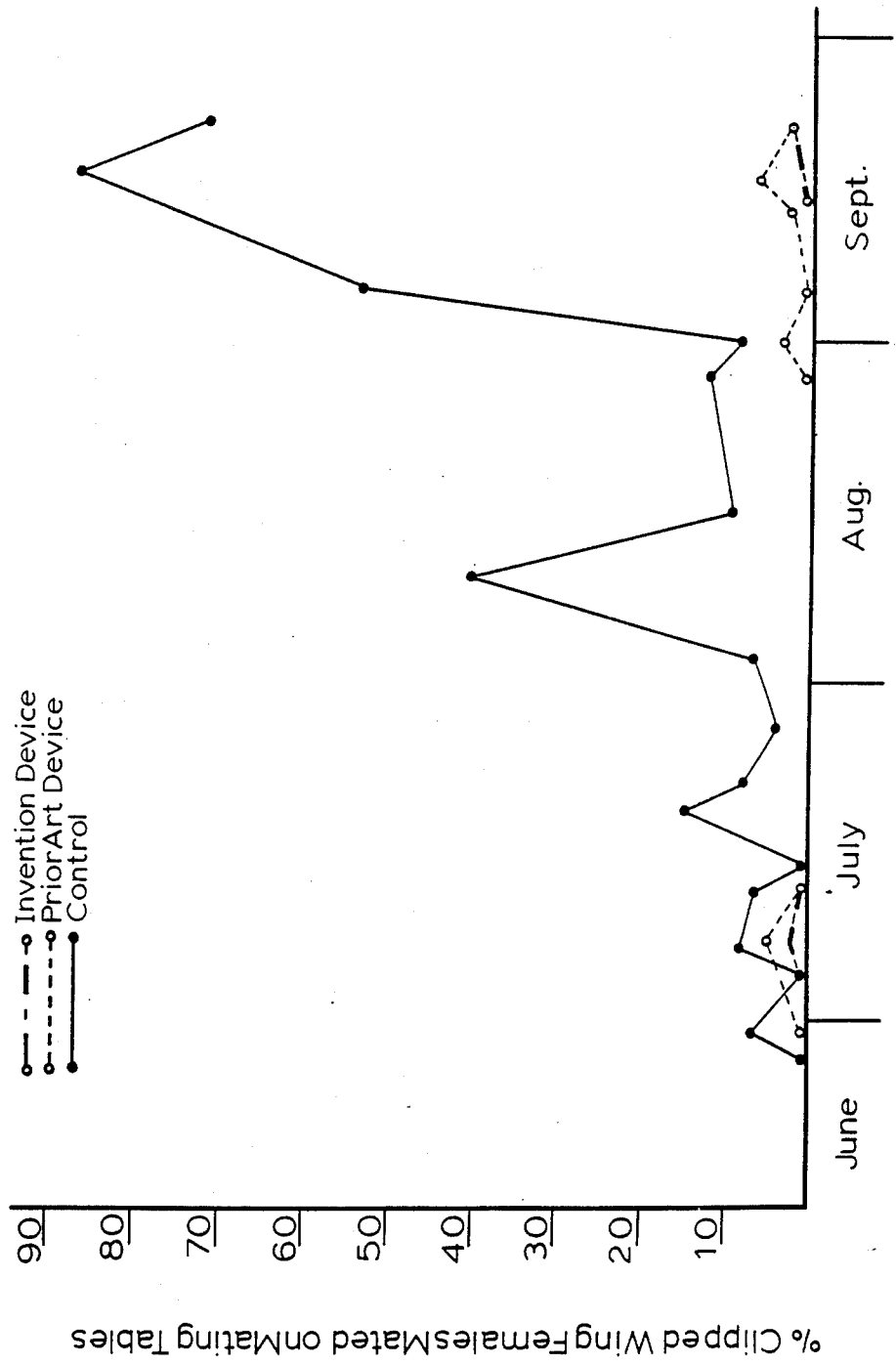
Figure 5:
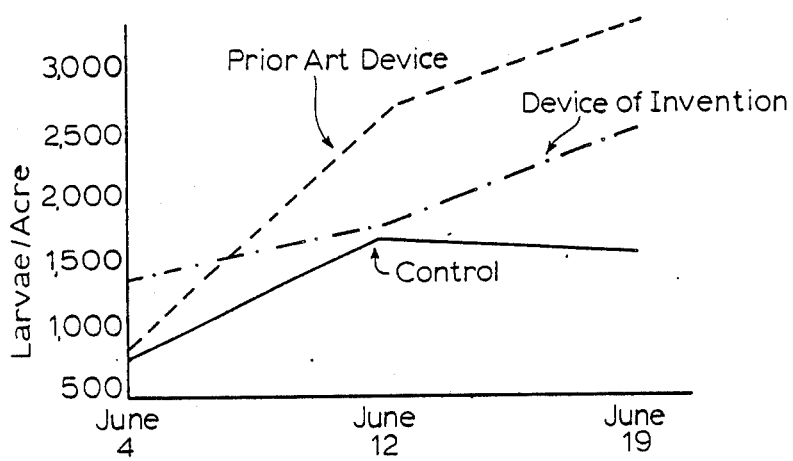
Figure 6:
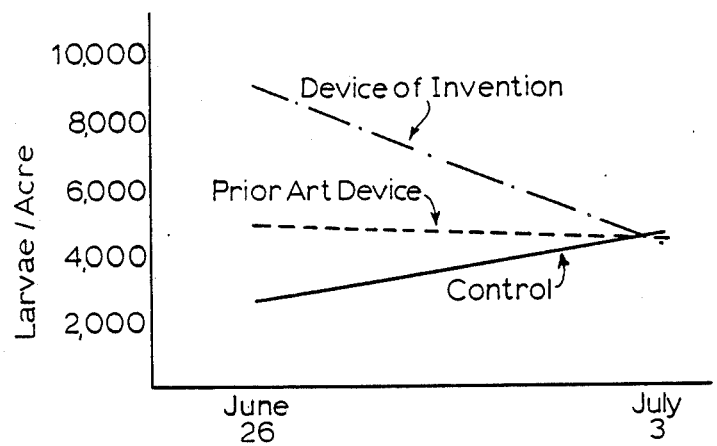

Following the observation period it was noted that there was minor reduction in mating activity (as determined by mating tables) and no significant differences in trap captures in the prior art device treatment compared to the invention device treatment. There was also a highly significant reduction in both mating and trap captures in treated versus untreated (conventional practice) plots. The average number of pink bollworm moths captured in the traps during the observation period in each of the fields is plotted graphically in FIG. 3 of the accompanying drawings. FIG. 4 shows graphically the number of clipped wing female moths mated during the observation period in each of the test fields. The graph shows that the overall density of moths in the area during the observation period was relatively low. One can therefore conclude from FIGS. 3 and 4 that at low population densities of the moths, there is no statistically significant difference between treatments with the prior art devices and the devices of the present invention.

EXAMPLE 2

In the Harquahala Valley area of Arizone, pin squares (Prefloral buds) were haphazardly sampled from a 100 acre interplanted Pima and Delta Pne variety stub cotton field and found to be at least 30% infested with pink bollworm moths. The field was divided into approximate thirds and one delta type pheromone trap was placed in each plot to monitor male pink bollworm moth flights.

Pre-treatment rosette (infested bloom) counts were made by systematically sampling the field in the following manner: one third into each plot from both the north and south side, a row was selected for sampling with only one provision; that the northern row be a Delta Pine row and the southern row be a Pima row. In each of the six rows (two per plot) five, three-hundred foot sections were staked and rosettes as well as the total number of flowers were counted. The percent infestation and density of larvae per acre could then be estimated.

The northern plot (or top third of the field) received no treatment. The central third of the field received an application of the prior art devices prepared as described in Example 1, supra., (calculated to be an application of 18 grams Nomate and 3 pints/acrs of Bio-tac). The southern third of the field received, in addition to the same amount of Nomate and Bio-tac, 0.21 oz./acre (or 0.0004 lbs. a.i./acre of Ambush in the form of the devices of the invention prepared as described in Example 1, supra.

Three and four weeks post-treatment, boll infestation counts were made by systematically sampling the field in the following manner: In each of the staked plots used for the pre-treatment rosette counts, the total number of susceptible (10-20 day old) bolls were counted. Fifty bolls were then collected from these plots and inspected for larval infestation. The percent infestation and density of larvae per acre could then be estimated.

Mating tables were conducted eight times post-treatment in the same manner as in Example 1, supra. Each plot had ten tables per plot, each with eight virgin females.

Infestation counts on the day of treatment showed that the plot to receive the dispersion of invention devices was twice as infested with moths as the other plots. The infestation counts on the first day are graphically shown in FIG. 5 of the accompanying drawings. Post-treatment counts revealed a 54.7% reduction in infestation levels (larvae per acre) in the plot treated with the devices of the invention. The prior art device treated plot revealed a drop in infestation of 9% compared to the control plot which increased in infestation by 25.4%. The counts following the treatment period are shown graphically in FIG. 6 of the accompanying drawings.

Mating tables show a dramatic difference among all three of the plots in terms of the number of females mated (see below).

| COMPARISON OF MATING TABLE RESULTS IN TREATED AND UNTREATED PLOTS | | | | |
|---|---|---|---|---|
| | Mated | Not Mated | Total | % Females Mated |
| Control | 198 | 335 | 533 | 37% |
| Prior Art Device | 82 | 461 | 543 | 15% |
| Device of the Invention | 37 | 475 | 512 | 7% |
| Total | 317 | 1271 | 1588 | |

One can conclude from this example that at high population densities there is a significant difference amont prior art and inventive devices and untreated plots. This difference is seen in both infestation and mating table data. The use of Ambush in the Bio-tac coating apparently decreased the number of males available to accidentally encounter females, thereby increasing the effectiveness of pheromone mating disruption in suppression of pest populations.

Those skilled in the art will appreciate that many modifications of the above-described preferred embodiments of the invention may be made without departing from the spirit and the scope of the invention. As will be appreciated from the examples given above, one preferred embodiment is the device wherein the insecticide is in admixture with the adhesive sticking agent, the sticking agent being one which is an insufficient adhesive to adhere the insect selected for attraction, to the coated device. This permits the insecticide dosed insect after contact with the device to leave the situs of the device. The advantages include not interrupting the contact of other insects with the device and the carrying of insecticide to nests, etc., where other insects of the same species may be dosed by contact with the carrier insect.

What is claimed is:

1. In a device for attracting selected insects to a predetermined situs, and dosing the attracted insect with an insecticidal amount of an insecticide for the insects, which comprises;
    a body of a synthetic, polymeric resin for the containment of a pheromone which is an attractant for one of the male and the female sex gender of the selected insects;
    said pheromone, contained within the body; and
    means for the controlled release of the pheromone for containment in the form of a vapor, at a rate so as to attract the one of the male and female insect;
    the improvement, which comprises;
    a coating on at least a portion of the outside of the body, of an insecticidally effective amount of an insecticide for the insects mixed with an adhesive sticking agent, said agent being insufficient to adhere the insects to the coated device.

2. A method for killing selected insects at a predetermined situs, which comprises;
    dispersing at said situs a device for attracting and killing said insects, which comprises;
    a body of synthetic, polymeric resin for the containment of a chemical compound which is an attractant for one of the male and the female sex gender of the selected insects;
    said compound, contained within the body;
    means for the controlled release of the compound from containment, in the form of a vapor, at a rate so as to attract the one of the male and female insect; and
    a coating on at least a portion of the outside of the body, of an insecticidally effective amount of an insecticide for the insects in admixture with an adhesive sticking agent;
    whereby an insect is attracted to said situs by the vapor, comes in contact with said device, receives a dose of said insecticide through adhered admixture and is free to leave said situs with adhered admixture.

3. In a device for attracting selected insects to a predetermined situs, and dosing the attracted insect with an insecticidal amount of an insecticide for the insects, which comprises;
    a capillary tubular filament;
    a pheromone of the selected insect, contained in the filament for controlled vapor release therefrom; and
    a sticking agent on the outer surface of the filament;
    the improvement which comprises, an effective amount of an insecticide for the insect, deposited on the outer surface of the filament in admixture with the sticking agent, said sticking agent being an insufficient adhesive for adhering the insects to the device.

* * * * *